US006596754B1

(12) United States Patent
Hara et al.

(10) Patent No.: US 6,596,754 B1
(45) Date of Patent: Jul. 22, 2003

(54) PREVENTIVES/REMEDIES FOR MULTIPLE ORGAN FAILURE

(75) Inventors: Tsuyoshi Hara, Tokyo (JP); Kazuko Fujiwara, Tokyo (JP)

(73) Assignee: Daiichi Pharmaceuticals Co., Ltd., Tokyo (JP)

( * ) Notice: Subject to any disclaimer, the term of this patent is extended or adjusted under 35 U.S.C. 154(b) by 0 days.

(21) Appl. No.: 09/786,236

(22) PCT Filed: Sep. 3, 1999

(86) PCT No.: PCT/JP99/04783
§ 371 (c)(1),
(2), (4) Date: Mar. 2, 2001

(87) PCT Pub. No.: WO00/13707
PCT Pub. Date: Mar. 16, 2000

(30) Foreign Application Priority Data

Sep. 3, 1998 (JP) .......................................... 10/249492

(51) Int. Cl.⁷ ....................... A61K 31/40; C07D 207/09
(52) U.S. Cl. ....................... 514/422; 514/423; 514/367; 514/373; 514/375
(58) Field of Search ................................ 514/423, 422, 514/367, 373, 375

(56) References Cited

U.S. PATENT DOCUMENTS 5,576,343 A * 11/1996 Nagahara et al.

FOREIGN PATENT DOCUMENTS

EP 0 540 051 5/1993

OTHER PUBLICATIONS

Tanaka et al., The effect of heparin on multiple oran failure . . . , database–caplus, AN 1991:74953, abstract, Thromb. Res., 1990, vol. 60(4), pp. 321–330.*
Dickneite., Influence of C1–inhibitor . . . , Database–Caplus, AN 1994:242299, abstract, Behring Inst. Mitt, 1993, vol93, pp. 299–305.*
Siebeck et al., Hirudin prevents intravascular coagulation . . . , Database–Caplus, AN 1988:448187, abstract, Chir. Forum Exp. Klin. Forsch, 1988, pp. 297–300.*
E. F. Mammen, et al., Journal of Antimicrobial Chemotherapy, vol. 41, Suppl. A, pp. 17–24, "The Haematological Manifestations of Sepsis", Jan. 1998.
B. Eisele, et al., Seminars in Thrombosis and Hemostasis, vol. 24, No. 1, pp. 71–80, "Clinical Experience with Antithrombin III Concentrates in Critically III Patients with Sepsis and Mulitple Organ Failure", 1998.
G. Dickneite, Seminars in Thrombosis and Hemostasis, vol. 24, No. 1, pp. 61–69, "Antithrombin III in Animal Models of Sepsis and Organ Failure", 1998.
M. Howard, et al., J. Exp. Med., vol. 177, No. 4, pp. 1205–1208, "Interleukin 10 Protects Mice Form Lethal Endotoxemia", 1993.
K. Irita, et al., Journal of Surgical Research, vol. 56, pp. 216–220, "The Limiting Effect of Dichloroacetate on Endotoxin–Induced Liver Damage in Starved Rats", 1994.
M. Siebeck, Chemical Abstracts, vol. 127, No. 8, AN 103799, Mech. Ther. Approaches, vol. 2, Issue Pt. 2, pp. 1210–1217, "Thrombin Inhibition, Immune Consequences Trauma, Shock Sepsis", 1994.

* cited by examiner

Primary Examiner—William R. A. Jarvis
Assistant Examiner—Vickie Kim
(74) Attorney, Agent, or Firm—Oblon, Spivak, McClelland, Maier & Neustadt, P.C.

(57) ABSTRACT

The present invention relates to a preventive and/or therapeutic drug for hypercytokinemia, liver diseases, and syndromes caused by the aggravation of sepsis, containing an anti-thrombin agent and/or a thrombin production inhibitor as an active ingredient. The present invention is applicable to prevention of or therapy for diseases such as sepsis, severe sepsis, septic shock, and multiple organ dysfunction syndrome. More particularly, the present invention is useful for an emergency medical service, for treatment of injury caused by a traffic accident, burns, heat attacks, or severe infective diseases. In addition, the present invention is useful for prevention and treatment for hypercytokinemia and liver diseases.

13 Claims, 1 Drawing Sheet

PREVENTIVES/REMEDIES FOR MULTIPLE ORGAN FAILURE

BACKGROUND OF THE INVENTION

1. Field of the Invention

The present invention relates to a pharmaceutical, and more particularly to a preventive and/or therapeutic drug for hypercytokinemia, liver diseases, and syndromes caused by the aggravation of sepsis.

2. Background Art

Previously, sepsis was understood to refer to systemic aggravation resulting from invasion of bacteria into blood (bacteremia) and, for example, organ failure caused thereby. At one time it seemed that no effective remedy for sepsis existed, but since the 1980s sepsis has been treated positively. Recently, sepsis has come to be defined as the onset of systemic inflammatory response syndrome (SIRS) caused by an infective disease, and has become a target of medical treatment (Igakunoayumi, Vol. 181, No. 1, p 3–7; Apr. 5, 1997).

Sepsis is known to increase the concentration of various cytokines in blood, causing hypercytokinemia.

In addition, progress of sepsis may cause severe sepsis, septic shock, and multiple organ dysfunction syndrome (MODS).

Prevention and treatment for diseases comprising sepsis and syndromes caused by the aggravation of sepsis including multiple organ dysfunction syndrome are very important to emergency medical service, for treatment of injury caused by traffic accident, burns, heat attacks, and severe infective diseases, and therefore, development of an effective drug is desired.

Accordingly, an object of the present invention is to provide a preventive or therapeutic drug for diseases comprising sepsis and syndromes caused by the aggravation of sepsis.

SUMMARY OF THE INVENTION

The present inventors have performed extensive studies by use of a lipopolysaccharide intravenous injection model (Nikkyukyuikaishi, 1994: 5: p1–14) known as an animal test model for sepsis and septic shock, and have found that an anti-thrombin agent and/or a thrombin production inhibitor; more specifically, a blood coagulation factor Xa inhibitor, exhibits an excellent effect in affording protection against sepsis and septic shock and an excellent effect in affording prevention of and therapy for hypercytokinemia and liver diseases. The present invention has been accomplished based on this finding.

Accordingly, the present invention provides a preventive and/or therapeutic drug for a syndrome caused by the aggravation of sepsis, containing an anti-thrombin agent and/or a thrombin production inhibitor as an active ingredient.

The present invention also provides a preventive and/or therapeutic drug for hypercytokinemia, containing an anti-thrombin agent and/or a thrombin production inhibitor as an active ingredient.

The present invention also provides a preventive and/or therapeutic drug for liver diseases, containing an anti-thrombin agent and/or a thrombin production inhibitor as an active ingredient.

The present invention also provides use of an anti-thrombin agent and/or a thrombin production inhibitor for producing a preventive and/or therapeutic drug for a syndrome caused by the aggravation of sepsis.

The present invention also provides use of an anti-thrombin agent and/or a thrombin production inhibitor for producing a preventive and/or therapeutic drug for hypercytokinemia.

The present invention also provides use of an anti-thrombin agent and/or a thrombin production inhibitor for producing a preventive and/or therapeutic drug for liver diseases.

The present invention also provides a method of treatment of a syndrome caused by the aggravation of sepsis, wherein an anti-thrombin agent and/or a thrombin production inhibitor is administered to a patient in need thereof.

The present invention also provides a method of treatment of hypercytokinemia, wherein an anti-thrombin agent and/or a thrombin production inhibitor is administered to a patient in need thereof.

The present invention also provides a method of treatment of a liver disease, wherein an anti-thrombin agent and/or a thrombin production inhibitor is administered to a patient in need thereof.

DETAILED DESCRIPTION OF PREFERRED EMBODIMENTS

Figure 1:
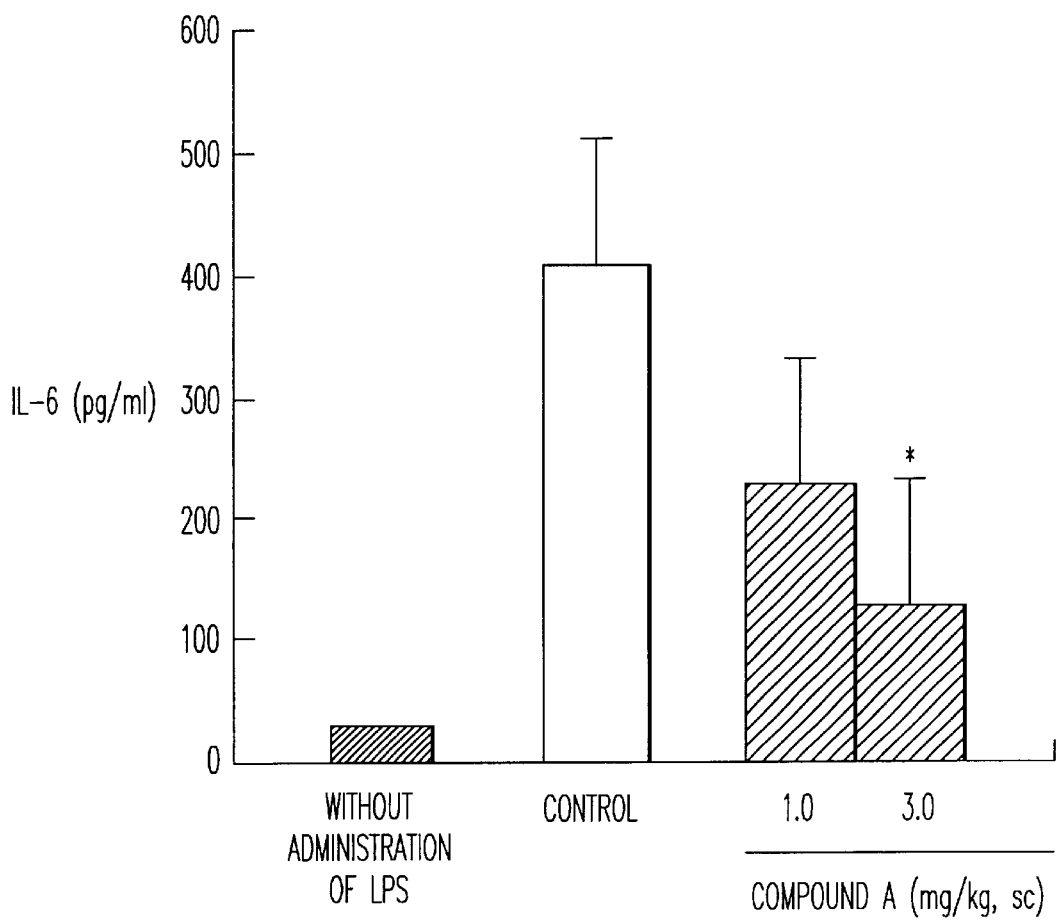
FIG. 1 shows the effect of Compound A against hypercytokinemia.

In the drug of the present invention, no particular limitation is imposed on anti-thrombin agents and/or thrombin production inhibitors serving as active ingredients, so long as they inhibit the activity of thrombin. Examples of the inhibitors include thrombin inhibitors, blood coagulation factor Xa inhibitors, and blood coagulation factor VIIa inhibitors.

Examples of thrombin inhibitors include synthesized anti-thrombin agents; specifically, Argatroban. Examples of blood coagulation factor Xa inhibitors include the compounds represented by the below-described formula, DZ-4927 (product of Zeneca Co.), and the compounds described in DE Patent No. 19530996 and EP patent application No. 0842941 A1. Examples of blood coagulation factor VIIa inhibitors include Corsevein (product of Corvas Co.).

Among the above-described inhibitors, thrombin production inhibitors and blood coagulation factor Xa inhibitors are preferable. Among the blood coagulation factor Xa inhibitors, preferred ones are an aromatic amidine derivative of formula (1), a salt of the derivative, a solvate of the derivative, and a solvate of the salt of the derivative.

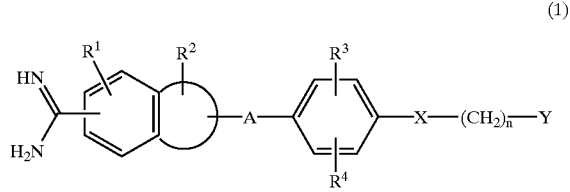

(1)

[wherein $R^1$ represents a hydrogen atom or a lower alkoxyl group;

$R^2$ represents a hydrogen atom, a lower alkyl group, a lower alkoxyl group, a carboxyl group, an alkoxycarbonyl group, a carboxyalkyl group, or an alkoxycarbonylalkyl group;

R³ represents a hydrogen atom, a carboxyl group, an alkoxycarbonyl group, a carboxyalkyl group, an alkoxycarbonylalkyl group, a carboxyalkoxyl group or an alkoxycarbonylalkoxyl group;

R⁴ represents a hydrogen atom, a halogen atom, an amino group, a cyano group, a nitro group, a hydroxyl group, a lower alkyl group, or a lower alkoxyl group;

n represents a number between 0 and 4 inclusive; and

A represents a C1–C4 alkylene group optionally substituted by one or two hydroxyalkyl groups, carboxyl groups, alkoxycarbonyl groups, carboxyalkyl groups, or alkoxycarbonylalkyl groups, or a group represented by the following formula;

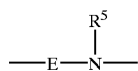

(wherein E represents a lower alkylene group or a carbonyl group and R⁵ represents a hydrogen atom or a group represented by formula —D—W—R⁶ (wherein D is a group represented by

(wherein Z is an oxygen atom or a sulfur atom), a group represented by

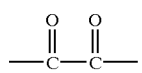

or a sulfonyl group;

W represents a single bond or a group represented by —NR⁷ -(wherein R⁷ represents a hydrogen atom, a carbamoyl group, a lower alkoxycarbonyl group, a mono- or di-lower alkylaminocarbonyl group, a lower alkylsulfonyl group, a mono- or di-lower alkylaminothiocarbonyl group, a lower alkyl group which may have a substituent, or a lower alkanoyl group which may have a substituent); and R⁶ represents a hydroxyl group, a lower alkoxyl group, a lower alkyl group which may have a substituent, an aryl group which may have a substituent, or a heteroaryl group which may have a substituent)};

X represents a single bond, an oxygen atom, a sulfur atom, or a carbonyl group;

Y represents a saturated or unsaturated 5- or 6-membered heterocyclic or cyclic hydrocarbon group which may have a substituent, an amino group which may have a substituent, or an aminoalkyl group which may have a substituent; and the group represented by

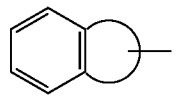

represents a group selected from among indolyl, benzofuranyl, benzothienyl, benzimidazolyl, benzoxazolyl, benzothiazolyl, naphthyl, tetrahydronaphthyl, or indanyl].

Japanese Patent Application Laid-Open (kokai) No. 208946/1993 and WO 96/16940 disclose that the above-described aromatic amidine derivatives of formula (1), salts of the derivatives, solvates of the derivatives, and solvates of the salts of the derivatives inhibit blood coagulation factor Xa and are useful as blood coagulation depressants and preventive and therapeutic drugs against thrombus.

In the above-described formula (1), examples of the lower alkyl groups include C1–C6 linear, branched, and cyclic alkyl groups. Specific examples thereof include a methyl group, an ethyl group, a propyl group, an isopropyl group, a butyl group, a secondary butyl group, a tertiary butyl group, a pentyl group, a hexyl group, a cyclopropyl group, a cyclobutyl group, a cyclopentyl group, and a cyclohexyl group.

The lower alkyl group may contain a substituent, and examples of the substituents include a halogen atom, a carboxyl group, a carbamoyl group, an amino group, a cyano group, a nitro group, a lower alkanoyl group, a lower alkoxyl group, a lower alkoxycarbonyl group, a mono- or di-lower alkylamino group, an aryl group, an aralkyloxy group, an aryloxy group, a mercapto group, a lower alkylthio group, a lower alkylthiocarbonyl group, a hydroxyl group, a carbamoyl group, and a mono- or di-lower alkylaminocarbonyl group.

Examples of the lower alkoxyl groups include a C1–C6 alkoxyl group, and specific examples include a methoxyl group, an ethoxyl group, a propoxyl group, an isopropoxyl group, a butoxyl group, a secondary butoxyl group, and a tertiary butoxyl group.

Examples of the alkoxycarbonyl groups include a methoxycarbonyl group, an ethoxycarbonyl group, a propoxycarbonyl group, and a butoxycarbonyl group.

Examples of the carboxyalkyl groups include a carboxymethyl group, a carboxyethyl group, and a carboxypropyl group.

Examples of the alkoxycarbonylalkyl groups include a methoxycarbonylmethyl group, an ethoxycarbonylmethyl group, a propoxycarbonylmethyl group, a methoxycarbonylethyl group, an ethoxycarbonylethyl group, a methoxycarbonylpropyl group, and an ethoxycarbonylpropyl group.

Examples of the carboxyalkoxyl groups include a carboxymethoxyl group, a carboxyethoxyl group, and a carboxypropoxyl group. Examples of the alkoxycarbonylalkoxyl groups include a methoxycarbonylmethoxyl group, an ethoxycarbonylmethoxyl group, a propoxycarbonylmethoxyl group, a methoxycarbonylethoxyl group, and an ethoxycarbonylethoxyl group.

Examples of the hydroxyalkyl groups include a hydroxymethyl group, a hydroxyethyl group, a hydroxypropyl group, and a hydroxybutyl group. Examples of the C1–C4 alkylene groups include a methylene group, an ethylene group, a trimethylene group, and a tetramethylene group.

Examples of the mono- or di-lower alkylaminocarbonyl groups include mono-lower alkylaminocarbonyl groups such as a methylaminocarbonyl group, an ethyaminocarbonyl group, a propylaminocarbonyl group, an isopropylaminocarbonyl group, a butylaminocarbonyl group, an isobutylaminocarbonyl group, a pentylaminocarbonyl group, an isopentylaminocarbonyl group, a hexylaminocarbonyl group, and an isohexylaminocarbonyl group. Examples of the di-alkylaminocarbonyl groups include symmetric dialkylaminocarbonyl groups having two same lower alkyl groups as substituents such as a dimethylaminocarbonyl group, a diethylaminocarbonyl group, a dipropylaminocarbonyl group, a diisopropylaminocarbonyl group, a dibutylaminocarbonyl group, and a dipentylaminocarbonyl group; and asymmetric dialkylaminocarbonyl groups having two different lower alkyl groups as substituents such as an ethylmethylaminocarbonyl group, a methylpropylaminocarbonyl group, an ethylpropylaminocarbonyl group, a butylmethylaminocarbonyl group, a butylethylaminocarbonyl group, and a butylpropylaminocarbonyl group.

Examples of the lower alkylsulfonyl groups include a methylsulfonyl group, an ethylsulfonyl group, a propylsulfonyl group, an isopropylsulfonyl group, a butylsulfonyl group, an isobutylsulfonyl group, a pentylsulfonyl group, an isopentylsulfonyl group, a hexylpropyl group, and an isohexylpropyl group.

With regard to the mono- or di-lower alkylaminothiocarbonyl groups, examples of the mono-lower alkylaminothiocarbonyl groups include a methylaminothiocarbonyl group, an ethylaminothiocarbonyl group, a propylaminothiocarbonyl group, an isopropylaminothiocarbonyl group, a butylaminothiocarbonyl group, an isobutylaminothiocarbonyl group, a pentylaminothiocarbonyl group, an isopentylaminothiocarbonyl group, a hexylaminothiocarbonyl group, and an isohexylaminothiocarbonyl group. Examples of the dialkylaminothiocarbonyl groups include symmetric dialkylaminothiocarbonyl groups having two same lower alkyl groups as substituents such as a dimethylaminothiocarbonyl group, a diethylaminothiocarbonyl group, a dipropylaminothiocarbonyl group, a diisopropylaminothiocarbonyl group, a dibutylaminothiocarbonyl group, or a dipentylaminothiocarbonyl group; and asymmetric dialkylaminotiocarbonyl groups having two different lower alkyl groups as substituents such as an ethylmethylaminothiocarbonyl group, a methylpropylaminothiocarbonyl group, an ethylpropylaminothiocarbonyl group, a butylmethylaminothiocarbonyl group, a butylethylaminothiocarbonyl group, or a butylpropylaminothiocarbonyl group.

Examples of the lower alkanoyl groups include a formyl group, an acetyl group, a propionyl group, a butyryl group, an isobutyryl group, a valeryl group, an isovaleryl group, a pivaloyl group, and a hexanoyl group. Of these, an acetyl group, a propionyl group, and a butyryl group are preferred, with an acetyl group and a propionyl group being more preferred. The lower alkanoyl group may have a substituent.

Examples of groups which may serve as a substituent for the lower alkanoyl group include a halogen atom, a carboxyl group, a carbamoyl group, an amino group, a cyano group, a nitro group, a lower alkanoyl group, a lower alkoxyl group, a lower alkoxycarbonyl group, a mono- or di-lower alkylamino group, an aryl group, an aralkyloxy group, an aryloxy group, a mercapto group, a lower alkylthio group, a lower alkylthiocarbonyl group, a hydroxyl group, a carbamoyl group, and a mono- or di-lower alkylaminocarbonyl group.

Examples of the aryl groups include a phenyl group, a naphthyl group, a biphenyl group, and an anthryl group. The aryl group may contain a substituent.

Examples of the heteroaryl groups include a furyl group, a thienyl group, a pyrolyl group, an imidazolyl group, a pyrazolyl group, an isothiazolyl group, an isoxazolyl group, a pyridyl group, a pyrimidinyl group, a quinolyl group, an isoquinolyl group, a quinazolinyl group, a quinolidinyl group, a quinoxalinyl group, a cinnolinyl group, a benzimidazolyl group, an imidazopyridyl group, a benzofuranyl group, a naphthylidinyl group, a 1,2-benzoisoxazolyl group, a benzoxazolyl group, a benzothiazolyl group, an oxazolopyridyl group, an isothiazolopyridyl group, and a benzothienyl group. Of these, a furyl group, a thienyl group, a pyrolyl group, an imidazolyl group, and a pyridyl group are preferred. The aryl group may have a substituent.

Examples of groups which may serve as a substituent of these aryl or heteroaryl groups include a halogen atom, a carboxyl group, an amino group, a cyano group, a nitro group, a hydroxyl group, a lower alkoxyl group, a lower alkoxycarbonyl group, a mono- or di-lower alkylamino group, a lower alkanoyl group, and a lower alkyl group optionally having a substituent.

Preferably, the saturated or unsaturated 5- or 6-membered heterocyclic group is a heterocyclic group having 1 or 2 nitrogen or oxygen atoms. Specific examples of the heterocycles include pyrrolidine, piperidine, imidazoline, piperazine, tetrahydrofuran, hexahydropyrimidine, pyrrole, imidazole, pyrazine, pyrrolidinone, piperidinone, and morpholine. Examples of the saturated or unsaturated cyclic hydrocarbon groups include a cyclopentyl group and a cyclohexyl group. Examples of the aminoalkyl groups include an aminomethyl group, an aminoethyl group, and an aminopropyl group.

The heterocyclic groups and cyclic hydrocarbon groups may have a substituent. Examples of the groups which may serve as a substituent of the heterocyclic groups or cyclic hydrocarbon groups include a lower alkyl group, a lower alkanoyl group, a carbamoyl group, a monoalkylcarbamoyl group, a dialkylcarbamoyl group, a formimidoyl group, an alkanoimidoyl group, a benzimidoyl group, a carboxyl group, an alkoxycarbonyl group, a carboxyalkyl group, an alkylcarbonylalkyl group, an aminoalkyl group, an alkanoylamino group, an alkanoylaminoalkyl group, an imino group, and an alkoxycarbonylimino group.

Examples of groups which may substitute for the amino moiety of the amino group and aminoalkyl group include a lower alkyl group, a pyrrolidinyl group, a pyrazyl group, a carbamoyl group, a monoalkylcarbamoyl group, a dialkylcarbamoyl group, a lower alkanoyl group, a formimidoyl group, an alkanoimidoyl group, a benzimidoyl group, and an alkoxycarbonyl group.

The above-described groups such as an alkyl group, an alkoxyl group, and an alkanoyl group, and an alkyl moiety, an alkoxyl moiety, and an alkanoyl moiety of these groups preferably have 1 to 6 carbon atoms.

The group represented by

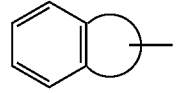

is preferably selected from among benzofuranyl, benzimidazolyl, indolyl, benzothienyl, benzothiazolyl, naphthyl, or tetrahydronaphthyl.

The aromatic amidine derivatives represented by formula (1) according to the present invention, salts of the derivatives, solvates of the derivatives, and solvates of the salts of the derivatives may have an asymmetric carbon atom. In this case, optical isomers, stereoisomers, and mixtures thereof attributed to the asymmetric carbon atom are all within the scope of the present invention.

In the present invention, among the above-described aromatic amidine derivatives represented by formula (1), salts of the derivatives, solvates of the derivatives, and solvates of the salts of the derivatives, the following compounds and salts or solvates thereof are particularly preferred:

2-[4-[((3S)-1-acetimidoyl-3-pyrrolidinyl)oxy]phenyl]-3-(7-amidino-2-naphthyl)propionic acid, (+)-2-[4-[((3S)-1-acetimidoyl-3-pyrrolidinyl)oxy]phenyl]-3-(7-amidino-2-naphthyl)propionic acid, (2S)-2-[4-[((3S)-1-acetimidoyl-3-pyrrolidinyl)oxy]phenyl]-3-(7-amidino-2-naphthyl)propionic acid, (2R)-2-[4-[((3R)-1-acetimidoyl-3-pyrrolidinyl)oxy]phenyl]-3-(7-amidino-2-naphthyl)propionic acid, 2-[4-[(1-acetimidoyl-4-piperidyl)oxy]phenyl]-3-(7-amidino-2-naphthyl)propionic acid, (+)-2-[4-[(1-acetimidoyl-4-piperidyl)oxy]phenyl]-3-(7-amidino-2-naphthyl)propionic acid, 2-[4-[(1-acetimidoyl-4-piperidyl)oxy]phenyl]-3-(5-amidinobenzo[b]thien-2-yl)propionic acid, 2-[4-[((2S)-1-acetimidoyl-2-pyrrolidinyl)methoxy]phenyl]-3-(5-amidinobenzo[b]thien-2-yl)propionic acid, (+)-2-[4-[((2S)-1-acetimidoyl-2-pyrrolidinyl)methoxy]phenyl]-3-(5-amidinobenzo[b]thien-2-yl)propionic acid, 3-[4-[((3S)-1-acetimidoyl-3-pyrrolidinyl)oxy]phenyl]-4-(5-amidinobenzo[b]thien-2-yl)butyric acid, 2-[4-[((3S)-1-acetimidoyl-3-pyrrolidinyl)oxy]phenyl]-3-(6-amidino-1-ethyl-2-indolyl)propionic acid, 2-[4-[((3R)-1-acetimidoyl-3-pyrrolidinyl)oxy]phenyl]-3-(6-amidino-1-ethyl-2-indolyl)propionic acid, 2-[4-[(1-acetimidoyl-4-piperidinyl)oxy]phenyl]-3-(6-amidino-1-ethyl-2-indolyl)propionic acid, N-[4-[(1-acetimidoyl-4-piperidyl)oxy]phenyl]-N-[(7-amidino-2-naphthyl)methyl]-N'-methylsulfamide, ethyl N-[N-4-[(1-acetimidoyl-4-piperidyl)oxy]phenyl]-N-[(7-amidino-2-naphthyl)methyl]sulfamoyl] carbamate, 4-[N-4-[(1-acetimidoyl-4-piperidyl)oxy]phenyl]-N-[(7-amidino-2-naphthyl)methyl]sulfamoyl]benzoic acid, N-[4-[(1-acetimidoyl-4-piperidyl)oxy]phenyl]-N-[(7-amidino-2-naphthyl)methyl]sulfamoylacetic acid, ethyl N-[N-[4-[(1-acetimidoyl-4-piperidyl)oxy]phenyl]-N-[(7-amidino-2-naphthyl)methyl]sulfamoyl] glycinate, N-[N-4-[(1-acetimidoyl-4-piperidyl)oxy]phenyl]-N-[(7-amidino-2-naphthyl)methyl]sulfamoyl]-N-ethoxycarbonylglycine, and N-[N-4-[(1-acetimidoyl-4-piperidyl)oxy]phenyl]-N-[(7-amidino-2-naphthyl)methyl]sulfamoyl]glycine.

Particularly preferred ones are:

(2S)-2-[4-[((3S)-1-acetimidoyl-3-pyrrolidinyl)oxy]phenyl]-3-(7-amidino-2-naphthyl)propionic acid, (+)-2-[4-[(1-acetimidoyl-4-piperidyl)oxy]phenyl]-3-(7-amidino-2-naphthyl)propionic acid, (+)-2-[4-[((2S)-1-acetimidoyl-2-pyrrolidinyl)methoxy]phenyl]-3-(5-amidinobenzo[b]thien-2-yl)propionic acid, ethyl N-[N-[4-[(1-acetimidoyl-4-piperidyl)oxy]phenyl]-N-[(7-amidino-2-naphthyl)methyl]sulfamoyl] glycinate, and N-[N-4-[(1-acetimidoyl-4-piperidyl)oxy]phenyl]-N-[(7-amidino-2-naphthyl)methyl]sulfamoyl]glycine, and N-[4-[(1-acetimidoyl-4-piperidyl)oxy]phenyl]-N-[(7-amidino-2-naphthyl)methyl]sulfamoylacetic acid.

Furthermore, the following compounds are also preferred:

(2S)-2-[4-[((3S)-1-acetimidoyl-3-pyrrolidinyl)oxy]phenyl]-3-(7-amidino-2-naphthyl)propionic acid hydrochloride pentahydrate, (+)-2-[4-[(1-acetimidoyl-4-piperidyl)oxy]phenyl]-3-(7-amidino-2-naphthyl) propionic acid dihydrochloride, (+)-2-[4-[((2S)-1-acetimidoyl-2-pyrrolidinyl)methoxy]phenyl]-3-(5-amidinobenzo[b]thien-2-yl)propionic acid dihydrochloride, ethyl N-[N-[4-[(1-acetimidoyl-4-piperidyl)oxy]phenyl]-N-[(7-amidino-2-naphthyl)methyl]sulfamoyl]glycinate dihydrochloride, N-[N-4-[(1-acetimidoyl-4-piperidyl)oxy]phenyl]-N-[(7-amidino-2-naphthyl)methyl]sulfamoyl]glycine dihydrochloride, and N-[4-[(1-acetimidoyl-4-piperidyl)oxy]phenyl]-N-[(7-amidino-2-naphthyl)methyl]sulfamoylacetic acid dihydrochloride.

As is described below, the above-described compound of formula (1), which is a blood coagulation factor Xa inhibitor (a type of an anti-thrombin agent and/or a thrombin production inhibitor), exhibits an excellent effect against sepsis model with the intravenous injection of a lipopolysaccharide which dies of multi organ dysfunction syndrome caused by sepsis. Therefore, an anti-thrombin agent and/or a thrombin production inhibitor are useful as a preventive and therapeutic agent for a syndrome caused by the aggravation of sepsis.

A drug of the present invention is directed to prevention or treatment for sepsis; i.e. systemic inflammatory response syndrome (SIRS) accompanying an infective disease. Examples of syndromes caused by the aggravation of sepsis include severe sepsis, septic shock, and multiple organ dysfunction syndrome.

An animal model for the above-described intravenous injection of lipopolysaccharide is also known as a hypercytokinemia model (Nikkyukyuigakukaishi, 1994: 5: p 1–14). In this model, an anti-thrombin agent and/or a thrombin production inhibitor exhibits an effect in therapy for hypercytokinemia; particularly, in decrease of IL-6. Such an effect against hypercytokinemia is considered a mechanism of an anti-thrombin agent and/or a thrombin production inhibitor against a syndrome caused by the aggravation of sepsis.

The present inventors studied changes in parameters of liver functions in the above-described animal model of lipopolysaccharide intravenous injection. Subsequently, they found that this model may be used as a model for liver diseases, since, as compared with a control, this model exhibits significant increases in GOT, GPT, LDH (lactic acid dehydrogenase), and T-BIL (total bilirubin). In addition, the present inventors studied an action of an anti-thrombin agent and/or a thrombin production inhibitor against this model. Based on significantly improved liver function parameters (GOT, GPT, LDH, and T-BIL), they found that these agents are useful as a preventive and therapeutic agent for liver diseases.

The drug of the present invention can be administered orally and parenterally. The dose of the drug of the present invention may be appropriately increased or decreased in accordance with the symptoms, age, and weight of a patient. For example, when the compound of formula (1) is administered orally, an appropriate dose thereof is 5–1000 mg/day, preferably, 10–500 mg/day for an adult. The compound may be administered in tablet, capsule, powder, or granule form. By means of blending with customary additives, such as excipients, lubricants, and binders, the compound can be processed into drug products by known methods. When the compound of formula (1) is administered subcutaneously by intravenous injection or intravenous drip infusion, an appropriate dose is 0.1–100 mg/day, preferably 0.5–30 mg/day, for an adult. In addition, the compound of formula (1) can be administered percutaneously. When a percutaneous administration agent is produced from the compound, as a percutaneous absorption promoter, there are preferably incorporated one or more ingredients selected from the group consisting of higher alcohols, higher alkanes, higher fatty acids, polyhydric alcohol fatty acid esters, terpenes, alkyl sulfates, alkylamine oxides, carboxybetaines, polyoxyalkylene alkyl ethers, sulfoxides, and amides.

EXAMPLES

The present invention will next be described in more detail by way of examples, which should not be construed as limiting the invention thereto.

Example 1
(Sepsis, Septic Shock, and Multiple Organ Dysfunction Syndrome)
(1) Method Rats (Slc: Wistar, male, 10 weeks old, n=15) were anesthetized by halothane. Subsequently, lipopolysaccharide (LPS) (*E. coli*, O55: B5) (20 mg/2 ml/kg) was administered to each rat through the femoral vein. Immediately after administration, (2S)-2-[4-([(3S)-1-acetimidoyl-3-pyrrolidinyl]oxy)phenyl]-3-(7-amidino-2-naphthyl) propionic acid hydrochloride pentahydrate (hereinafter referred to as "Compound A") was subcutaneously administered to each rat at a dose of 0.3, 1, or 3 mg/kg. The mortality for the rats was observed 24 hours after the administration of LPS.

(2) Results

As is apparent from Table 1, whereas the mortality for the rats in a control group was 100%, the groups administered Compound A at doses of 0.3, 1, and 3 mg/kg exhibited mortality of 80, 40, and 7%, respectively, demonstrating that Compound A dose-dependently decreases the mortality for rats ($\chi^2$ test: p<0.001).

TABLE 1

Decrease in mortality in an LPS intravenous administration shock model

|  | Dose (mg/kg) | Mortality | Mortality in terms of percentage(%) |
|---|---|---|---|
| Control |  | 15/15 | 100 |
| Compound A | 0.3 | 12/15 | 80 |
|  | 1 | 6/15 | 40 |
|  | 3 | 1/15 | 7 |

Example 2
(Hypercytokinemia)
(1) Method

Rats (Slc: Wistar, male, 10 weeks old, n=7) were anesthetized by halothane. Subsequently, LPS (*E. coli*, O55: B5) (20 mg/2 ml/kg) was administered to each rat through the femoral vein. Immediately after administration, compound A was subcutaneously administered to each rats at a dose of 1 or 3 mg/kg. Six hours after administration of LPS, blood was collected from the abdominal aorta in the presence of citric acid, and plasma IL-6 was measured by ELISA.

(2) Results

FIG. 1 shows the concentration of plasma IL-6 six hours after administration of LPS. As is apparent from FIG. 1, compound A dose-dependently suppressed the increase in concentration of IL-6 after the administration of LPS (#p <0.1).

Example 3
(Liver Disease)
(1) Method

Rats (Slc: Wistar, male, 10 weeks old, n=7) were anesthetized by halothane. Subsequently, LPS (*E. coli*, O55: B5) (20 mg/2 ml/kg) was administered to each rat through the femoral vein. Immediately after administration, compound A was subcutaneously administered to each rat at a dose of 0.3, 1, or 3 mg/kg. Six hours after LPS administration, blood was collected from the abdominal aorta in the presence of citric acid, and the blood was collected to measurement of liver function parameters (GOT, GPT, LDH, and T-BIL).

(2) Results

Table 2 shows the concentrations of GOT, GPT, LDH, and T-BIL measured six hours after administration of LPS. As is apparent from Table 2, compound A dose-dependently suppressed the increase in each liver function parameter after administration of LPS.

TABLE 2

|  | GOT (IU/L) | GPT (IU/L) | LDH (IU/L) | TBIL (mg/dl) |
|---|---|---|---|---|
| Without administration of LPS | 73 ± 3 | 55 ± 3 | 67 ± 13 | 0.05 ± 0.002 |
| Control | 3404 ± 406 | 3716 ± 496 | 23847 ± 3225 | 0.46 ± 0.15 |
| Compound A |  |  |  |  |
| (0.3 mg/kg) | 1939 ± 442 | 1986 ± 467 * | 11560 ± 2983 | 0.48 ± 0.22 |
| (1 mg/kg) | 1183 ± 281 *** | 1216 ± 352 *** | 6297 ± 2291 *** | 0.20 ± 0.10 ** |
| (3 mg/kg) | 364 ± 42 *** | 189 ± 22 *** | 972 ± 186 *** | 0.10 ± 0.01 *** |

Mean ± S.E. (n = 7);
* refers to p < 0.05,
** refers to p < 0.01, and
*** refers to P < 0.001 with respect to control (Tukey multiple comparison).

The present invention is applicable to prevention of or therapy for diseases such as sepsis, severe sepsis, septic shock, and multiple organ dysfunction syndrome. More particularly, the present invention is useful for an emergency medical service, for treatment of injury caused by a traffic accident, burns, heat attacks, or severe infective diseases. In addition, the present invention is useful for prevention of and therapy for hypercytokinemia and liver diseases.

What is claimed is:

1. A method for the treatment of a syndrome caused by the aggravation of sepsis, comprising administering an effective amount of a compound of formula (1) or a salt or solvate of a compound of formula (1) to a subject in need thereof, wherein formula (1) is:

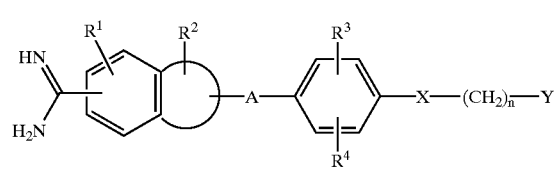

(1)

wherein
R$^1$ represents a hydrogen atom or a lower alkoxy group;
R$^2$ represents a hydrogen atom, a lower alkyl group, a lower alkoxy group, a carboxyl group, an alkoxycarbonyl group, a carboxyalkyl group, or an alkoxycarbonylalkyl group;

$R^3$ represents a hydrogen atom, a carboxyl group, an alkoxycarbonyl group, a carboxyalkyl group, an alkoxycarbonylalkyl group, a carboxyalkoxyl group or an alkoxycarbonylalkoxyl group;

$R^4$ represents a hydrogen atom, a halogen atom, an amino group, a cyano group, a nitro group, a hydroxyl group, a lower alkyl group, or a lower alkoxyl group;

n represents a number between 0 and 4 inclusive; and

A represents:

a $C_1$–$C_4$ alkylene group optionally substituted by one or two hydroxyalkyl group(s), carboxyl group(s), alkoxycarbonyl group(s), carboxyalkyl group(s), or alkoxycarbonylalkyl group(s), a group represented by the following formula:

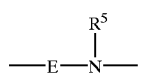

wherein E represents a lower alkylene group or a carbonyl group and $R^5$ represents a hydrogen atom or a group represented by formula —D—W—$R^6$, wherein D is a group represented by

and Z is an oxygen atom or a sulfur atom, a group represented by

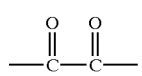

or a sulfonyl group;

wherein W represents a single bond or a group represented by —$NR^7$—, wherein $R^7$ represents a hydrogen atom, a carbamoyl group, a lower alkoxycarbonyl group, a mono- or di-lower alkylaminocarbonyl group, a lower alkylsulfonyl group, a mono- or di-lower alkylaminothiocarbonyl group, a lower alkyl group which may have a substituent, or a lower alkanoyl group which may have a substituent; and wherein $R^6$ represents a hydroxyl group, a lower alkoxyl group, a lower alkyl group which may have a substituent, an aryl group which may have a substituent, or a heteroaryl group which may have a substituent;

X represents a single bond, an oxygen atom, a sulfur atom, or a carbonyl group;

Y represents a saturated or unsaturated 5- or 6-membered heterocyclic or cyclic hydrocarbon group which may have a substituent, an amino group which may have a substituent, or an aminoalkyl group which may have a substituent; and

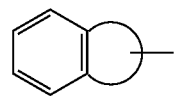

is selected from the group consisting of indolyl, benzofuranyl, benzothienyl, benzimidazolyl, benzoxazolyl, benzothiazolyl, naphthyl, tetrahydronaphthyl, and indanyl.

2. The method of claim 1 comprising administration of a compound of formula (1) that is an anti-thrombin agent.

3. The method of claim 1 comprising administration of a compound of formula (1) that is a thrombin production inhibitor.

4. The method of claim 1 comprising administration of a compound of formula (1) that is a blood coagulation factor Xa inhibitor.

5. The method of claim 1 comprising administration of a compound of formula (1) that is (2S)-2-[4-([[((3S)-1-acetimidoyl-3-pyrrolidinyl)oxy]phenyl]-3-(7-amidino-2-naphthyl)propionic acid hydrochloride pentahydrate.

6. The method of claim 1, wherein said syndrome is caused by the aggravation of sepsis.

7. The method of claim 1 comprising the treatment of multiple organ dysfunction syndrome.

8. The method of claim 1 comprising the treatment of severe sepsis.

9. The method of claim 1 comprising the treatment of septic shock.

10. The method of claim 1 that comprises oral administration of the compound of formula (1).

11. The method of claim 1 that comprises parenteral administration of the compound of formula (1).

12. The method of claim 1 that comprises intravenous administration of the the compound of formula (1).

13. A method for the treatment of a disease caused by the aggravation of sepsis, comprising administering an effective amount of a compound of formula (1) or a salt or solvate of a compound of formula (1) to a subject in need thereof, wherein formula (1) is:

(1)

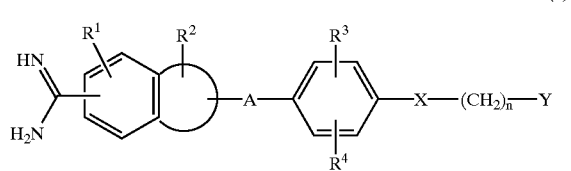

wherein $R^1$ represents a hydrogen atom or a lower alkoxy group, $R^2$ represents a hydrogen atom, a lower alkyl group, a lower alkoxy group, a carboxyl group, an alkoxycarbonyl group, a carboxyalkyl group, or an alkoxycarbonylalkyl group, $R^3$ represents a hydrogen atom, a carboxyl group, an alkoxycarbonyl group, a carboxyalkyl group, an alkoxycarbonylalkyl group, a carboxyalkoxyl group or an alkoxycarbonylalkoxyl group;

$R^4$ represents a hydrogen atom, a halogen atom, an amino group, a cyano group, a nitro group, a hydroxyl group, a lower alkyl group, or a lower alkoxyl group;

n represents a number between 0 and 4 inclusive; and

A represents:

a $C_1$–$C_4$ alkylene group optionally substituted by one or two hydroxyalkyl group(s), carboxyl group(s), alkoxycarbonyl group(s), carboxyalkyl group(s), or alkoxycarbonylakyl group(s), a group represented by the following formula:

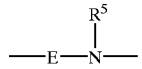

wherein E represents a lower alkylene group or a carbonyl group and $R^5$ represents a hydrogen atom or a group represented by formula —D—W—$R^6$, wherein D is a group represented by

and Z is an oxygen atom or a sulfur atom, a group represented by

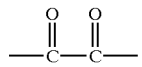

or a sulfonyl group;

wherein W represents a single bond or a group represented by —$NR^7$—, wherein $R^7$ represents a hydrogen atom, a carbamoyl group, a lower alkoxycarbonyl group, a mono- or di- lower alkylaminocarbonyl group, a lower alkylsulfonyl group, a mono- or di-lower alkylaminothiocarbonyl group, a lower alkyl group which may have a substituent, or a lower alkanoyl group which may have a substituent; and wherein $R^6$ represents a hydroxyl group, a lower alkoxyl group, a lower alkyl group which may have a substituent, an aryl group which may have a substituent, or a heteroaryl group which may have a substituent;

X represents a single bond, an oxygen atom, a sulfur atom, or a carbonyl group;

Y represents a saturated or unsaturated 5- or 6-membered heterocyclic or cyclic hydrocarbon group which may have a substituent, an amino group which may have a substituent, or an aminoalkyl group which may have a substituent; and

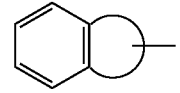

is selected from the group consisting of indolyl, benzofuranyl, benzothienyl, benzimidazolyl, benzoxazolyl, benzothiazolyl, naphtyl, tetrahydronaphthyl, and indanyl, wherein said disease is selected from the group consisting of sepsis, septic shock, hypercytokinemia and a liver disease.

* * * * *

UNITED STATES PATENT AND TRADEMARK OFFICE
CERTIFICATE OF CORRECTION

PATENT NO. : 6,596,754 B1
DATED : July 22, 2003
INVENTOR(S) : Hara et al.

It is certified that error appears in the above-identified patent and that said Letters Patent is hereby corrected as shown below:

<u>Title page,</u>
Item [73], Assignee, should read:
-- [73]  Assignee:  Daiichi Pharmaceutical Co., Ltd.,
Tokyo (JP) --

Signed and Sealed this

Fourth Day of November, 2003

JAMES E. ROGAN
*Director of the United States Patent and Trademark Office*